United States Patent [19]

Stahly

[11] Patent Number: 4,804,772

[45] Date of Patent: Feb. 14, 1989

[54] GEM-DISUBSTITUTED CYCLOHEXADIENONES AND THEIR PRODUCTION

[75] Inventor: G. Patrick Stahly, Baton Rouge, La.

[73] Assignee: Ethyl Corporation, Richmond, Va.

[21] Appl. No.: 177,097

[22] Filed: Apr. 4, 1988

[51] Int. Cl.$^4$ .............................. C07F 7/18; C07F 7/10
[52] U.S. Cl. .................................... 556/436; 556/418; 544/229; 549/215
[58] Field of Search ............... 556/436, 418; 544/229; 549/215

[56] References Cited

U.S. PATENT DOCUMENTS

| | | | |
|---|---|---|---|
| 2,920,092 | 1/1960 | Bailey | 556/436 |
| 3,472,888 | 10/1969 | Bazouin et al. | 556/436 X |
| 4,210,596 | 2/1980 | Cella | 556/436 |
| 4,238,401 | 12/1980 | Cella et al. | 556/436 |
| 4,360,686 | 11/1982 | Wang et al. | 556/436 X |
| 4,375,548 | 3/1983 | Wang | 556/470 |
| 4,448,980 | 5/1984 | Sogah | 556/436 X |
| 4,634,787 | 1/1987 | Wang | 556/470 |

OTHER PUBLICATIONS

Fujita et al., J. Am. Chem. Soc., 1985, 107, 4085–4087.

Primary Examiner—Paul F. Shaver
Attorney, Agent, or Firm—John F. Sieberth

[57] ABSTRACT

Quinones may be perfluoroalkylated by means of perfluoroalkyltrihydrocarbyl silane using certain active alkali metal salt catalysts devoid of fluorine (e.g., $LiN_3$, $NaN_3$, $KN_3$, NaCN KCN, CsCN, NaOH, KOH, $K_2CO_3$, and $Cs_2CO_3$). The reaction—which is conducted under essentially anhydrous conditions, preferably in a suitable liquid phase reaction medium, most preferably a dipolar aprotic solvent—results in the formation of gem-disubstituted cyclohexadienones in which the gem substituents are a perfluoroalkyl group and a trihydrocarbylsiloxy group. These gem-disubstituted compounds in turn can be readily converted to perfluoroalkyl substituted aromatics, thus circumventing the traditional need for photochlorination followed by halogen exchange using hydrogen fluoride as a means of preparing perfluoroalkyl aromatic compounds.

50 Claims, No Drawings

GEM-DISUBSTITUTED CYCLOHEXADIENONES AND THEIR PRODUCTION

TECHNICAL FIELD

This invention relates in general to perfluoroalkyl aromatic compounds. More particularly, this invention relates to a new class of perfluoroalkyl substituted compounds from which perfluoroalkyl aromatic compounds can be readily produced and to novel methods by which such perfluoroalkyl substituted compounds may be prepared.

BACKGROUND

Perfluoroalkyl aromatic compounds such as benzotrifluoride, 4-chlorobenzotrifluoride and 3-aminobenzotrifluoride are used in the production of a variety of products such as pharmaceuticals, crop protection chemicals, germicides, dyes, and the like. The classical method of forming trifluoromethyl aromatics involves the photochemical side-chain chlorination of a methyl aromatic compound to form a perchloromethyl substituted aromatic which in turn is reacted with hydrogen fluoride to effect an exchange of fluorine atoms for the chlorine atoms on the methyl group. Ortho- and para-trifluoromethylphenols and anilines are even more difficult to make. They have been synthesized by photochemical side-chain chlorination or bromination of the appropriate nitrotoluene to form the perhalomethyl nitrobenzene. This product is treated with hydrogen fluoride to form the perfluoromethyl nitrobenzene, which is then reduced to the perfluoromethyl aniline. Diazotization and hydrolysis of the latter forms the perfluoromethyl phenol.

In Example 6 of U.S. Pat. No. 4,634,787, Wang reports that reaction between quinone and trichloromethyltrimethylsilane in tetrahydrofuran using tetrabutylammonium fluoride as catalyst yielded 4-(trichloromethyl)-4-(trimethylsilyloxy)-2,5-cyclohexadien-1-one While the patentee refers to compounds having a —CX$_3$ group in which each X is independently halo, according to the patentee:

". . . preferably, each X is independently chloro or bromo. More preferably, each X is the same and is chloro or bromo. Even more preferably, each X is chloro. Preferred silanes [used as reactants in the process]are trichloromethylsilanes and the most preferred silane is trichloromethyltrimethylsilane."

THE INVENTION

In accordance with this invention there is provided a new class of perfluoroalkyl substituted compounds from which a wide variety of perfluoroaromatic compounds can readily be prepared. In addition, this invention provides a novel catalytic process by which these new perfluoroalkyl substituted compounds can be prepared.

This invention is in part based on the discovery that quinones may be perfluoroalkylated by means of perfluoroalkyltrihydrocarbyl silane using certain active alkali metal salt catalysts devoid of fluorine. The reaction results in the formation of gem-disubstituted cyclohexadienones in which the gem substituents are a perfluoroalkyl group and a trihydrocarbylsiloxy group. These gem-disubstituted compounds in turn can be readily converted to perfluoroalkyl substituted aromatics. Thus this invention circumvents the traditional need for photochlorination followed by halogen exchange using hydrogen fluoride as a means of preparing perfluoroalkyl aromatic compounds.

It is interesting to note that NaF and CaF$_2$, two of the fluoride ion catalysts recommended in U.S. Pat. No. 4,634,787 for use as catalysts are ineffective as catalysts in the perfluoroalkylation process of this invention.

The process of this invention is conducted under essentially anhydrous conditions, preferably in a suitable liquid phase reaction medium. The preferred solvents or liquid reaction media for use in the process are dipolar aprotic solvents such as N,N-dimethylformamide, N,N-diethylformamide, N,N-dimethylacetamide, sulfolane, acetonitrile, hexamethylphosphoramide, nitrobenzene, dimethylsulfoxide, N-methylpyrrolidone, and the like. When performing the reaction in a substantially anhydrous aprotic solvent of low polarity such as tetrahydrofuran, 1,4-dioxane or the like, it is desirable to utilize a phase transfer catalyst such as a crown ether. See in this connection C. M. Starks and C. Liotta, *Phase Transfer Catalysts*, Academic Press, 1978.

A variety of alkali metal salt catalysts devoid of fluorine may be used in the practice of this invention provided they exhibit the appropriate catalytic activity. In this connection, not all fluorine-free alkali metal salts exhibit a catalytic effect in the reaction and thus in any given instance where the suitability of a given fluorine-free alkali metal salt is not known, recourse should be had to the simple expedient of performing a few pilot experiments to determine whether the material will serve as a catalyst in the reaction.

Alkali metal salts devoid of fluorine which are active catalysts in the process of this invention include the alkali metal azides such as lithium azide, sodium azide, and potassium azide; alkali metal cyanides such as sodium cyanide, potassium cyanide, and cesium cyanide; alkali metal hydroxides such as sodium hydroxide and potassium hydroxide; alkali metal carbonates such as potassium carbonate and cesium carbonate; and the like.

It is not known how or why the catalysts function in the process of this invention. Nor, is the structure or composition of the actual catalytic species known. All that is known is that when the catalyst is added to the reaction system in the form of an inorganic salt such as above-described, preferably in finely divided form, the reaction proceeds. In the absence of the catalyst, no reaction occurs.

The most preferred catalysts are potassium cyanide and potassium carbonate, because of their high activity, ready availability, and low cost. Reactions performed in acetonitrile using potassium cyanide or potassium carbonate as the catalyst and in dimethylformamide with potassium carbonate as the catalyst have been found particularly efficacious.

Ordinarily the reaction will be conducted at temperatures within the range of about −20 to about 100° C., although temperatures outside this range may be found useful in particular cases. Preferably, the temperature is maintained within the range of about 0° to about 25° C. throughout substantially the entire reaction period.

Quinones that may be used in the process of this invention include mononuclear and polynuclear quinones, both 1,2-quinones and 1,4-quinones. Election donating substituents, such as hydrocarbyl groups, hydrocarbyloxy groups, amino and mono- and dihydrocarbylamino groups, the hydroxyl group, and the like may be present in the quinones. A few exemplary quinones which may be used include 1,2-benzoquinone, 1,4-benzoquinone, 2-methyl-1,4-benzoquinone, 2-methoxy-1,4-benzoquinone, 2,5-dimethoxy-1,4-benzoquinone, 2-anilino-1,4-benzoquinone, 2,5-dianilino-1,4-benzoquinone, 2-phenyl-1,4-benzoquinone, polyporic acid, the ubiquinones, 2,3-dimethyl-1,4-benzoquinone, 2,5-dimethyl-1,4-benzoquinone, 1,4-naphthoquinone, 1,2-naphthoquinone, Vitamin $K_1$, Vitamin $K_2$, 2-methyl-1,4-naphthoquinone, anthraquinone, 2-methylanthraquinone, 2-ethylanthraquinone, 2-tert-butylanthraquinone, 1-aminoanthraquinone, 2-aminoanthraquinone, 1-amino-4-hydroxyanthraquinone, 1,2-diaminoanthraquinone, 1,4-diaminoanthraquinone, 1,5-diaminoanthraquinone, 2,6-diaminoanthraquinone, 1,8-diamino-4,5-dihydroxyanthraquinone, 1-hydroxy-4-(p-toluidino)anthraquinone, diphenoquinone, indanthrene blue, 1,2-dihydroxyanthraquinone, 9,10-phenanthraquinone, indanthrene violet, chrysophanic acid, and the like.

The perfluoroalkyltrihydrocarbyl silanes used in the process of this invention may be represented by the general formula $$R'SiR_3$$

where R' is a perfluoroalkyl group (trifluoromethyl, pentafluoroethyl, perfluorohexyl, etc.) and R, independently, is a hydrocarbyl group (alkyl, alkenyl, alkynyl, cycloalkyl, aryl, aralkyl, etc.). The number of carbon atoms in R and R' is irrelevant so long as the silane is co-reactive with the quinone in the process. A few illustrative compounds include trifluoromethyltrimethylsilane, tridecyltrifluoromethylsilane, trifluoromethyltrivinylsilane, triallyltrifluoromethylsilane, tricyclopentyltrifluoromethylsilane, tricyclopropylcarbinyltrifluoromethylsilane, trifluoromethyltriphenylsilane, trifluoromethyltri-(1-naphthyl)silane, tribenzyltrifluoromethylsilane, and corresponding and similar analogs containing the higher "homologous" perfluoroalkyl groups such as perfluoroethyl, perfluoropropyl, perfluoroisopropyl, perfluorobutyl, etc.

As noted above, this invention also provides gem-disubstituted cyclohexadienones in which the gem substituents are a perfluoroalkyl group and a trihydrocarbylsiloxy group. In one preferred embodiment the perfluoroalkyl group is a trifluoromethyl group. In another preferred embodiment the trihydrocarbylsiloxy group is a trialkylsiloxy group. Particularly preferred compounds are those in which the gem substituents are a trialkylsiloxy group and a trifluoromethyl group.

Among the preferred subclasses of compounds provided by this invention are the following:
4-trialkylsiloxy-4-trifluoromethyl-2,5-cyclohexadien-1-ones;
4-trialkylsiloxy-4-trifluoromethyl-2,5-cyclohexadien-1-ones having an alkyl substituent in at least the 2 or 6 position;
1,4-dihydro-1-oxo-4-trialkylsiloxy-4-trifluoromethylnaphthalenes;
9,10-dihydro-9-oxo-10-trialkylsiloxy-10-trifluoromethylanthracenes;
2-trialkylsiloxy-2-trifluoromethyl-3,5-cyclohexadien-1-ones;
2-trialkylsiloxy-2-trifluoromethyl-3,5-cyclohexadien-1-ones having an alkyl substituent in at least the 4 or 6 position; and
9,10-dihydro-9-oxo-10-trialkylsiloxy-10-trifluoromethylphenanthrenes.

Illustrative gem-disubstituted compounds of this invention include:
4-trifluoromethyl-4-trimethylsiloxy-2,5-cyclohexadien-1-one;
4-pentafluoroethyl-4-trimethylsiloxy-2,5-cyclohexadien-1-one;
4-heptafluoropropyl-4-trimethylsiloxy-2,5-cyclohexadien-1-one;
4-tricyclohexylsiloxy-4-trifluoromethyl-2,5-cyclohexadien-1-one;
4-trifluoromethyl-4-triphenylsiloxy-2,5-cyclohexadien-1-one;
4-nonafluorobutyl-4-(4-biphenylyl)siloxy-2,5-cyclohexadien-1-one;
4-tribenzylsiloxy-4-trifluoromethyl-2,5-cyclohexadien-1-one;
2-ethyl-4-trifluoromethyl-4-tributylsiloxy-2,5-cyclohexadien-1-one;
4-trifluoromethyl-2-methoxy-4-trioctylsiloxy-2,5-cyclohexadien-1-one;
4-trifluoromethyl-2,5-dimethoxy-4-tri-(4-methylphenyl)siloxy-2,5-cyclohexadien-1-one; 2-anilino-4-pentafluoroethyl-4-trimethylsiloxy-2,5-cyclohexadien-1-one; 2-trifluoromethyl-2-triisopropylsiloxy-3,5-cyclohexadien-1-one;
6-ethyl-2-trifluoromethyl-2-tributylsiloxy-3,5-cyclohexadien-1-one;
4,6-diethyl-2-trifluoromethyl-2-triphenylsiloxy-3,5-cyclohexadien-1-one;
1,4-dihydro-1-oxo-4-trifluoromethyl-4-trioctylsiloxynaphthalene;
1,4-dihydro-2-methyl-1-oxo-4-trifluoromethyl-4-tripropylsiloxynaphtahalene;
9,10-dihydro-9-oxo-10-pentafluoroethyl-10-triethylsiloxyanthracene;
1,4-diamino-9,10-dihydro-9-oxo-10-pentafluoroethyl-10-triethylsiloxyanthracene;
9,10-dihydro-1,2-dihydroxy-9-oxo-10-pentafluoroethyl-10-triethylsiloxyanthracene;
9,10-dihydro-9-oxo-10-pentafluoroethyl-10-triethylsiloxyphenanthrene; and
9,10-dihydro-1-ethoxy-9-oxo-10-pentafluoroethyl-10-triethylsiloxyphenathrene.

The practice and advantages of this invention will become still further apparent from the following illustrative examples. Examples I and II illustrate the preparation of perfluoroalkyltrihydrocarbylsilanes, the class of reactants used in the process of this invention. The procedure used in Examples I and II is based on Ruppert, et al. *Tetrahedron Letters*, 1984, 25, 2195.

EXAMPLE I

Triethyltrifluoromethylsilane

A flask equipped with a dry ice condenser was flame dried under a nitrogen stream, and charged with 25g (0.17 mol) of chlorotriethylsilane and 40 mL of dichloromethane. After cooling the resulting solution to −78° C. and charging the condenser with dry ice and acetone, 40 mL (0.43 mol) of bromotrifluoromethane (Freon 13Bl) that had been condensed into a graduated tube was warmed to room temperature and allowed to distill into the flask. The cold solution was treated dropwise with 66mL (0.24 mol) of hexaethylphosphorous triamide, allowed to stir at −78° C. for two hours, and allowed to stir at room temperature overnight. Low boiling components were then short path distilled into a cold (−78° C.) receiving flask at >1 torr with the pot temperature kept at <50° C. The distillate was further fractionated by removal of the dichloromethane (40°–45° C. at atmospheric pressure) and short path distillation to give 22.0 g of 98% pure (69% yield) triethyltrifluoromethylsilane: bp 52°–54° C. at 10 torr; $^1$H NMR (CDCl$_3$)δ0.59–1.16 (m); $^{19}$F NMR (CDCl$_3$, relative to CFCl$_3$) −61.3 ppm (s); IR (neat) 2960, 2915, 2882, 1458, 1413, 1206, 1055 1020, 734, 693 cm$^{-1}$; mass spectrum (70 eV) m/z (relative intensity) 115 (66, M-CF$_3$), 105 (46), 87 (85), 77 (100), 59 (56), 49 (41), 47 (37), 41 (38). Anal. Calcd. for C$_7$H$_{15}$F$_3$Si: C, 45.62; H, 8.20. Found: C, 47.53; H, 8.56.

EXAMPLE II

Tri-n-butyltrifluoromethylsilane

A flask equipped with a dry ice condenser was flame dried under a nitrogen sream, and charged with 5.0g (20 mmol) of chlorotri-n-butylsilane and 10 mL of dichloromethane. After cooling the resulting solution to −78° C. and charging the condenser with dry ice and acetone, 6.2 mL (66 mmol) of bromotrifluoromethane (Freon 13Bl) that had been condensed into a graduated tube was warmed to room temperature and allowed to distill into the flask. The cooling bath was removed and the mixture was allowed to warm to the temperature of the refluxing Freon (−59° C.). To this cold solution was added, dropwise, 8.0 mL (29 mmol) of hexaethylphosphorous triamide. The resulting solution was stirred at reflux for 1 hour. Removal of the condenser and continued stirring for 1 hour resulted in evaporation of excess Freon and warming of the solution to room temperature. Dilution with 30 mL of dichloromethane, water (three 30 mL portions) and lN HCl (two 30 mL portions) washing, drying (MgSO$_4$), and concentration afforded a residue which was short path distilled to give 3.6 g (64% yield) of tri-n-butyltrifluoromethylsilane: bp 53°–58° C. at 0 5 torr; $^1$H NMR (CDCl$_3$)δ0.60–1.10 (m, 5H), 1.10–1.56 (m, 4H); $^{19}$F NMR (CDCl$_3$, relative to CFCl$_3$) −61.6 ppm (s); IR (neat) 2956, 2925, 2872, 1214, 1058 cm$^{-1}$; mass spectrum (70 eV) m/z (relative intensity) 199 (30, M-CF$_3$), 143 (80), 105 (30), 101 (27), 87 (30), 77 (66), 63 (43), 59 (41), 55 (54), 47 (25), 43 (20), 41 (100). Anal. Calcd. for C$_{13}$H$_{27}$F$_3$Si: C, 58.16; H, 10.14. Found: C, 58.26; H, 10.09.

Examples III through XIV illustrate the gem-disubstituted compounds of this invention and methods by which they may be prepared.

EXAMPLE III

4-Triethylsiloxy-4-trifluoromethyl-2,5-cyclohexadien-1-one

A mixture of 165 mg (1.5 mmol) of 1,4-benzoquinone, 332 mg (18 mmol) of triethyltrifluoromethylsilane, 15 mg (0.31 mmol) of sodium cyanide, and 2 mL of acetonitrile was stirred vigorously at 25° C. for 42 hours. The mixture was filtered and the filtrate was concentrated in vacuo. Purification of the resulting residue by preparative thin layer chromatography (one 2 mm silica gel plate eluted with 50% dichloromethane - 50% petroleum ether) afforded 178 mg (41% yield) of 4-triethylsiloxy-4-trifluoromethyl-2,5-cyclohexadien-1-one as a pale yellow liquid: bp 68°–78° C. at 0.5 torr; $^1$H NMR (CDCl$_3$)δ0.40–1.06 (m, 15H), 6.41 (d, 2H, J =9 Hz), 6.89 (d, 2H, J =9 Hz); $^{19}$F NMR (CDCl$_3$, relative to CFCl$_3$) −83.8 ppm (t, J$_{FH}$=4 Hz); IR (neat) 2956, 2912, 2877, 1677, 1611, 12.65, 12.40, 1182, 1129, 1067, 1004, 835, 749, 732 cm$^{-1}$; mass spectrum (70 eV) m/z (relative intensity) 263 (6, M-C$_2$H$_5$), 139 (79), 111 (100) 105 (68), 83 (41), 77 (100), 47 (31), 45 (35). Anal. Calcd. for C$_{13}$H$_{19}$F$_3$O$_2$Si: C, 53.39; H, 6.54. Found: C, 53.60; H, 6.79.

EXAMPLE IV

4-Triethylsiloxy-4-trifluoromethyl-2,5-cyclohexadien-1-one

The procedure of Example III was repeated except that the catalyst was 293 mg (4.5 mmol) of potassium cyanide and the reaction period was but one hour. The 4-triethylsiloxy-4-trifluoromethyl-2,5-cyclohexadien-1-one was recovered in 64

EXAMPLE V

4-Triethylsiloxy-4-trifluoromethyl-2,5-cyclohexadien-1-one

A mixture of 83 mg (0.77 mmol) of 1,4-benzoquinone, 1.66 mg (0.90 mmol) of triethyltrifluoromethylsilane, 92 mg (2.3 mmol) of powdered sodium hydroxide, and 1 mL of acetonitrile was stirred at 25° C. for 2 hours. The reaction mixture was poured into 20 mL of water and the resulting aqueous mixture was extracted with two 5 mL portions of dichloromethane. Combination, drying (MgSO$_4$), and concentration of the organic layers afforded a residue which was purified by PTLC, giving 66 mg (29% yield) of 4-triethylsiloxy-4-trifluoromethyl-2,5-cyclohexadien-1-one.

EXAMPLE VI

4-Triethylsiloxy-4-trifluoromethyl-2,5-cyclohexadien-1-one

A mixture of 83 mg (0.77 mmol) of 1,4-benzoquinone, 166 mg (0.90 mmol) of triethyltrifluoromethylsilane, 113 mg (2.3 mmol) of ground lithium azide, and 1 mL of acetonitrile was stirred at 25° C. for 22 hours. The reaction mixture was poured into 20 mL of 1N HCl and the resulting aqueous mixture was extracted with three 10 mL portions of dichloromethane. Combination, drying (MgSO$_4$), and concentration of the organic layers afforded a residue which was purified by PTLC, giving 96 mg (43% yield) of 4-triethylsiloxy-4-trifluoromethyl-2,5-cyclohexadien-1-one.

EXAMPLE VII

4-Triethylsiloxy-4-trifluoromethyl-2,5-cyclohexadien-1-one

The procedure of Example III was repeated using a mixture of 86 mg (0.80 mmol) of 1,4-benzoquinone, 147 mg (0.80 mmol) of triethyltrifluoromethylsilane, 22 mg (0.16 mmol) of potassium carbonate, and 1 mL of acetonitrile at 25° C. for 7 hours. PTLC afforded 120 mg (51% yield) of 4-triethylsiloxy-4-trifluoromethyl-2,5-cyclohexadien-1-one.

EXAMPLE VIII

4-Triethylsiloxy-4-trifluoromethyl-2,5-cyclohexadien-1-one

The procedure of Example VI was repeated using a mixture of 86 mg (0.80 mmol) of 1,4-benzoquinone, 147 mg (0.80 mmol) of triethyltrifluoromethylsilane, 22 mg (0.16 mmol) of potassium carbonate, and 1 mL of N,N-dimethylformamide at 25° C. for 1 hour. Extraction of the aqueous mixture with diethyl ether and PTLC afforded 123 mg (53% yield) of 4-triethylsiloxy-4-trifluoromethyl-2,5-cyclohexadien-1-one.

EXAMPLE IX 2,6-Di-tert-butyl-4-Triethylsiloxy-4-trifluoromethyl-2,5-cyclohexadien-1-one The procedure of Example III was repeated using a mixture of 176 mg (0.80 mmol) of 2,6-di-tert-butyl-1,4-benzoquinone, 147 mg (0.80 mmol) of triethyltrifluoromethylsilane, 22 mg (0.16 mmol) of potassium carbonate, and 1 mL of N,N-dimethylformamide at 25° C. for 21.5 hours. PTLC afforded 133 mg (41% yield) of 2,6-di-tert-butyl-4-triethylsiloxy-4-trifluoromethyl-2,5-cyclohexadien-1-one as a colorless liquid: $^1$H NMR (CDCl$_3$)δ0.39–1.10 (m, 15H), 1.22 (s, 18H), 6.50(s, 2H); $^{19}$F NMR (CDCl$_3$, relative to CFCl$_3$) −80.5 ppm (s); IR (neat) 2957, 2910, 2876, 1670, 1648, 1457, 1364, 1333, 1272, 1255, 1178, 1151, 1070, 1033, 994, 880, 845, 747 cm$^{-1}$; mass spectrum (70 eV) m/z (relative intensity) 375 (60, M-C$_2$H$_5$), 335 (50), 299 (20), 57 (100) 41 (40). Anal. Calcd. for C$_{21}$H$_{35}$F$_3$O$_2$Si: C, 62.34; H, 8.72. Found: C, 63.05; H, 8.75.

EXAMPLE X 4,6-Di-tert-butyl-2-Triethylsiloxy-2-trifluoromethyl-3,5-cyclohexadien-1-one The procedure of Example III was repeated using a mixture of 176 mg (0.80 mmol) of 3,5-di-tert-butyl-1,2-benzoquinone, 147 mg (0.80 mmol) of triethyltrifluoromethylsilane, 22 mg (0.16 mmol) of potassium carbonate, and 1 mL of acetonitrile at 25° C. for 24 hours. PTLC afforded 269 mg (83% yield) of 4,6-di-tert-butyl-2-triethylsiloxy-2-trifluoromethyl-3,5-cyclohexadien-1-one as a yellow liquid: $^1$H NMR (CDCl$_3$)δ0.35–1.10 (m, 15H), 1.16 (s, 3H), 1.23 (s, 3H), 5.85 (d, 1H, J =2 Hz), 6.84 (d, 1H, J=2 Hz); $^{19}$F NMR (CDCl$_3$, relative to CFCl$_3$) −80.0 ppm (s); IR (neat) 2955, 2909, 2874, 1689, 1459, 1366, 1270, 1244, 1179, 1143, 1072, 1033, 998, 890, 831, 810, 743, 695 cm$^{-1}$; mass spectrum (70 eV) m/z (relative intensity) 404 (29, M+), 389 (20), 375 (79, M-C$_2$H$_5$), 57 (100). Anal. Calcd. for C$_{21}$H$_{35}$F$_3$O$_2$Si: C, 62.34; H, 8.72. Found: C, 62.46; H, 8.69.

EXAMPLE XI 1,4-Dihydro-1-oxo-4-triethylsiloxy-4-trifluoromethylnaphthalene

The procedure of Example VIII was repeated using a mixture of 127 mg (0.80 mmol) of 1,4-naphthoquinone, 147 mg (0.80 mmol) of triethyltrifluoromethylsilane, 22 mg (0.16 mmol) of potassium carbonate, and 1 mL of N,N-dimethylformamide at 25° C. for 2 hours. PTLC afforded 113 mg (41% yield) of 1,4-dihydro-1-oxo-4-triethylsiloxy-4-trifluoromethylnaphthalene as a brown liquid: $^1$H NMR (CDCl$_3$)δ0.30–1.00 (m, 15H), 6.65 (d, 1H, J=10 Hz), 7.06 (d, 1H, J=10 Hz), 7.50-8.30 (m, 4 H); $^{19}$F NMR (CDCl$_3$, relative to CFCl$_3$) −79.6 ppm (s); IR (neat) 2956, 2911, 2876, 1676, 1599, 1454, 1379, 1299, 1253, 1178, 1154, 1110, 1065, 1058, 1018, 952, 836, 767, 748, 732 cm$^{-1}$; mass spectrum (70 eV) m/z (relative intensity) 313 (40, M-C$_2$H$_5$), 189 (55), 161 (100), 133 (55), 77 (30). Anal. Calcd. for C$_{17}$H$_{21}$F$_3$O$_2$Si: C, 59.62; H, 6.18. Found: C, 59.91; H, 6.33.

EXAMPLE XII 9,10-Dihydro-9-oxo-10-triethylsiloxy-10-trifluoromethylanthracene The procedure of Example VIII was repeated using a mixture of 167 mg (0.80 mmol) of 9,10-anthraquinone, 147 mg (0.80 mmol) of triethyltrifluoromethylsilane, 22 mg (0.16 mmol) of potassium carbonate, and 2 mL of N,N-dimethylformamide at 25° C. for 5 hours. PTLC afforded 258 mg (82% yield) of 9,10-dihydro-9-oxo--10-triethylsiloxy-10-trifluoromethylanthracene as a colorless liquid: $^1$H NMR (CDCl$_3$) δ 0.19–0.90 (m, 15H), 7.50–7.90 (m, 4H), 7.90–8.13 (m, 2H), 8.30–8.47 (m, 2H); $^{19}$F NMR (CDCl$_3$, relative to CFCl$_3$) −79.9 ppm (t, J$_{FH}$=14 Hz); IR (neat) 2959, 2931, 2875, 1667, 1589, 1455, 1412, 1320, 1272, 1245, 1179, 1134, 1087, 1012, 950, 932, 893, 841, 817, 763, 736, 715, 692, 662, 630, 596 cm$^{-1}$; mass spectrum (70 eV) m/z (relative intensity) 363 (10, M-C$_2$H$_5$), 211 (100), 183 (25), 77 (35). Anal. Calcd. for C$_{21}$H$_{23}$F$_3$O$_2$Si: C, 64.26; H, 5.91. Found: C, 64.26; H, 6.01.

EXAMPLE XIII 9,10-Dihydro-9-oxo-10-triethylsiloxy-10-trifluoromethylphenanthrene The procedure of Example VIII was repeated using a mixture of 167 mg (0.80 mmol) of 9,10-phenanthrenequinone, 147 mg (0.80 mmol) of triethyltrifluoromethylsilane, 22 mg (0.16 mmol) of potassium carbonate, and 2 mL of N,N-dimethylformamide at 25° C. for 4 hours. PTLC afforded 260 mg (83% yield) of 9,10-dihydro-9-oxo-10-triethylsiloxy-10-trifluoromethylphenanthrene as a pale yellow liquid: $^1$H NMR (CDCl$_3$) δ 0.45–1.17 (m, 15H), 7.31–8.10 (m, 8H); $^{19}$F NMR (CDCl$_3$, relative to CFCl$_3$) −79.4 ppm (s); IR (neat) 2953, 2909, 2874, 1707, 1598, 1450, 1298, 1279, 1251, 1230, 1178, 1117, 1029, 1009, 944, 918, 837, 778, 766, 757, 731, 630 cm$^{-1}$; mass spectrum (70 eV) m/z (relative intensity) 363 (49, M-C$_2$H$_5$), 294 (100), 236 (29). Anal. Calcd. for C$_{21}$H$_{23}$F$_3$O$_2$Si: C, 64.26; H, 5.91. Found: C, 64.28; H, 5.92.

EXAMPLE XIV

4-Tri-n-butylsiloxy-4-trifluoromethyl-2,5-cyclohexadien-1-one

A mixture of 86 mg (0.80 mmol) of 1,4-benzoquinone, 215 mg (0.80 mmol) of tri-n-butyltrifluoromethylsilane, 22 mg (0.16 mmol) of ground potassium carbonate, and 1 mL of N,N-dimethylformamide was stirred vigorously at room temperature for one hour and poured into 10 mL of IN HCl. The resulting aqueous mixture was extracted with three 10 mL portions of diethyl ether. Combination, drying (MgSO$_4$), and concentration of the ether layers afforded a residue which was purified by PTLC (one 2 mm silica gel plate eluted with 25% dichloromethane-75% petroleum ether) to give 156 mg (52% yield) of 4-tri-n-butylsiloxy-4-trifluoromethyl-2,5-cyclohexadien-1-one: $^1$H NMR (CDCl$_3$) δ 0.50–0.61 (m, 6H); 0.85 (t, 9H, J=5 Hz), 1.19–1.35 (m, 12H), 6.39 (d, 2H, J=9 Hz), 6.82 (d, 2H, J=9 Hz); $^{19}$F NMR (CDCl$_3$, relative to CFCl$_3$) −80.0 ppm (s); IR (neat) 2960, 2920, 2870, 2865, 1692, 1680, 1640, 1380, 1265, 1240, 1180, 1130, 1080, 1065, 1005, 990, 835, cm$^{-1}$; mass spectrum (70 eV) m/z (relative intensity) 319 (5, M-C$_4$H$_9$), 307 (48), 161 (20), 139 (39), 121 (52), 111 (75), 105 (62), 93 (72), 83 (29), 77 (100), 65 (24), 63 (50), 61 (24 55 (68), 44

(31), 43 (35), 41 (35). Anal. Calcd. for $C_{19}H_{31}F_3O_2Si$: C, 60.60; H, 8.30. Found: C, 60.76; H, 8.43.

Comparative Examples A and B presented below indicate that two of the fluorine containing catalysts recommended by Wang as effective in the reactions described in U.S. Pat. No. 4,634,787 are ineffective in the reactions of this invention.

COMPARATIVE EXAMPLE A

Attempted Use of Sodium Fluoride as Catalyst

A mixture of 83 mg (0.77 mmol) of 1,4-benzoquinone, 166 mg (0.90 mmol) of triethyltrifluoromethylsilane, and 1 mL of acetonitrile was treated with 97 mg (2.3 mmol) of sodium fluoride (dried at 180° C., 25 torr overnight) and stirred vigorously at room temperature for 3 days. A gas chromatographic analysis showed that no reaction occurred.

COMPARATIVE EXAMPLE B

Attempted Use of Calcium Fluoride as Catalyst

A mixture of 46 mg (0.4 mmol) of benzoquinone, 92 mg (0.5 mmol) of triethyltrifluoromethylsilane, 102 mg (1.3 mmol) of calcium fluoride, and 1 mL of acetonitrile was stirred at room temperature for 1 hour. A gas chromatographic analysis showed no reaction occurred.

The novel gem-disubstituted cyclohexadienones of this invention are eminently useful in the synthesis of a wide variety of perfluroalkyl substituted aromatic compounds, many of which are themselves novel and of considerable utility. For example, the gem-disubstituted cyclohexadienones can be reduced using suitable metal reductant systems to perfluoroalkylated phenols. Likewise, the cyclohexadienones of this invention can be subjected to reductive amination to produce perfluoroalkylated aromatic amines. Procedures useful in effecting such reductions and reductive aminations are illustrated in Examples XV through XIX below.

EXAMPLE XV

4-Trifluoromethylphenol

A solution of 300 mg (1.0 mmol) of 4-triethylsiloxy-4-trifluomethyl-2,5-cyclohexadien-1-one in 1 mL of absolute ethanol was treated successively with 134 mg (2.0 mmol) of zinc dust and 1 mL of a solution of 80% acetic acid - 20% water. The mixture was heated to reflux in a 120°±5° C. oil bath for one hour, allowed to cool to room temperature, and poured into 10 mL of water. The resulting aqueous mixture was extracted with three 10 mL portions of diethyl ether. Combination, drying (MgSO4), and concentration of the ether layers afforded a residue which was subjected to PTLC (one 2 mm plate eluted with 20% petroleum ether - 80% dichloromethane). Removal of the UV-active band from the plate afforded a mixture of triethylsilanol (23 area percent by gas chromatography) and 4-trifluoromethylphenol (71 area percent by gas chromatography): mass spectrum (70 eV) m/z (relative intensity) 162 (100, M+), 143 (56), 112 (31), 39 (22).

EXAMPLE XVI

2,6-Di-tert-butyl-4-trifluoromethylphenol

A strip of aluminum foil weighing 264 mg (9.8 mmol) was amalgamated by immersion in a solution of 2% mercuric chloride in water for 15 seconds, washed with absolute ehtanol followed by diethyl ether, cut into small pieces, and added to a solution of 412 mg of 96% pure (0.98 mmol) 2,6-di-tert-butyl-4-triethyl- siloxy-4-trifluoromethyl-2,5-cyclohexadien-1-one in 25 mL of 10% water - 90% tetrahydrofuran. The resulting mixture was heated at 70° C. for 1.5 hours, allowed to cool to room temperature, and filtered. The filter cake was washed with tetrahydrofuran. Concentration of the combined filtrates gave a residue which was poured into 25 mL of water. The aqueous mixture was extracted with three 10 mL portions of dichloromethane. Combination, drying (MgSO4), and concentration of the organic layers gave a residue which was purified by PTLC (one 2 mm silica gel plate eluted with petroleum ether), affording 247 mg of 95% pure (87% yield) 1,6-di-tert-butyl-4-trifluoromethylphenol. An analytical sample was obtained by crystallization from methanol: mp 78°-80° C.; $^1$H NMR (CDCl3) δ1.45 (s, 18H), 5.56 (broad s,1H), 7.50 (s,1H); $^{19}$F NMR (CDCl3, relative to CFCl3) −61.7 ppm (s); IR (KBr) 3632, 2963, 1337, 1319, 1241, 1167, 1141, 1109, 893, 668 cm$^{-1}$; mass spectrum (70 eV) m/z (relative intensity) 274 (20, M+), 259 (100), 231 (28), 57 (57), 41 (54). Anal. Calcd. for $C_{15}H_{21}F_3O$: C, 65.67; H, 7.72. Found: C, 65.46; H, 7.94.

EXAMPLE XVII

2,4-Di-tert-butyl-6-trifluoromethylphenol

A strip of aluminum foil weighing 267 mg (9.9 mmol) was amalgmated by immersion in a solution of 2% mercuric chloride in water for 15 seconds, washed with absolute ethanol followed by diethyl ether, cut into small pieces, and added to a solution of 400 mg (0.99 mmol) of 4,6-di-tert-butyl-2-triethylsiloxy-2-trifluoromethyl-3,5-cyclohexadien-1-one in 25 mL of 10% water -90% tetrahydrofuran. The resulting mixture was heated at 70° C. for 1.5 hours, allowed to cool to room temperature, and filtered. The filter cake was washed with 10 mL of tetrahydrofuran. Concentration of the combined filtrates gave a residue which was poured into 25 mL of water. The aqueous mixture was extracted with tree 10 mL portions of dichloromethane. Combination, drying and concentration of the organic layers gave a residue which was purified by PTLC (one 2 mm silica gel plate eluted with petroleum ether), affording 226 mg (83% yield) of 2,4-di-tert-butyl-6-trifluoromethylphenol as a colorless liquid: $^1$H NMR (CDCl3)δ1.31 (s, 9H), 1.45 (s, 9H), 5.56 (q,1H, $J_{HF}$=4 Hz), 7.39 (d,1H, J=2 Hz), 7.54 (d, 1H, J=2 Hz); IR (neat) 3624, 2959, 2906, 2868, 1481, 1458, 1448, 1363, 1340, 1263, 1251, 1170, 1126, 1097, 887, 694 cm$^{-1}$; mass spectrum (70 eV) m/z (relative intensity) 274 (20, M+), 259 (100), 239 (68), 98 (20), 57 (22), 41 (34).

EXAMPLE XVIII

4-Trifluoromethylphenol

A solution of 3.9 g (20 mmol) of 4-tri-n-butylsiloxy-4-trifluoromethyl-2,5-cyclohexadien-1-one in 10 mL of absolute ethanol was treated successively with 1.3 g (20 mmol) of zinc dust and 10 mL of a solution of 80% acetic acid - 20% water. The mixture was heated to reflux for one hour, allowed to cool to room temperature, and poured into 100 mL of water. The resulting aqueous mixture was extracted with three 50 mL portions of diethyl ether. Combination, drying (MgSO4), and concentration of the ether layers afforded a residue which purified by short path distillation at 5.0 torr. At 60°-65° C., 0.80 g (47% yield) of 4-trifluoromethylphenol was collected.

EXAMPLE XIX

4-Trifluoromethyl-1-naphthol

A strip of aluminum foil weighing 278 mg (10 mmol) was amalgamated by immersion in a solution of 2% mercuric chloride in water for 15 seconds, washed with absolute ethanol followed by diethyl ether, cut into small pieces, and added to a solution of 353 mg (1.0 mmol) of 1,4-dihydro-1-oxo-4-triethylsiloxy-4-trifluoromethylnaphthalene in 10 mL of 10% water - 90% tetrahydrofuran. The resulting mixture was heated at 70° C. for 1.5 hours, allowed to cool to room temperature, and filtered. The filter cake was washed with diethyl ether. Concentration of the combined filtrates gave a residue which was poured into 25 mL of water. The aqueous mixture was extracted with three 10 mL portions of dichloromethane. Combination, drying ($MgSO_4$), and concentration of the organic layers gave a residue which was purified by PTLC (one 2 mm silica gel plate eluted with dichloromethane), affording 90 mg (90% yield) of 4-trifluoromethyl-1-naphthol as a white solid. An analytical sample was obtained by recrystallization from dichloromethane-hexane: mp 132–133° C.; $^1$H NMR ($CDCl_3$) δ 5.50 (broad s,1H), 6.79 (d,1H, J=8Hz), 7.50–7.80 (m, 3H), 8.10–8.45 (m, 2H); $^{19}$F NMR ($CDCl_3$, relative to $CFCl_3$) -59.5 ppm (s); IR (KBr) 3327, 1580, 1385, 1355, 1327, 1260, 1251, 1241, 1195, 1178, 1146, 1120, 1111, 1101, 1056, 767, cm$^{-1}$; mass spectrum (70 eV) m/z (relative intensity) 212 (100, M$^+$), 133 (32), 115 (100). Anal. Calcd. for $C^{11}H_7F_3O$: C, 62.27; H, 3.33. Found: C, 61.82; H, 3.50.

EXAMPLE XX

4-Trifluoromethylaniline

A mixture of 400 mg (1.4 mmol) of 4-triethylsiloxy-4-trifluoromethyl-2,5-cyclohexadien-1-one, 572 mg (4.2 mmol) of ethyl glycinate hydrochloride, 298 mg (3.6 mmol) of sodium bicarbonate, and 10 mL of 95% ethanol was heated to reflux for 6 hours, allowed to cool to room temperature, and poured into 25 mL of water. The resulting aqueous mixture was extracted with three 10 mL portions of dichloromethane. The organic layers were combined and extracted with six 5 mL portions of 1N HCl. Combination of the aqueous layers and treatment with solid sodium bicarbonate until neutral to pH paper gave a cloudy mixture that was extracted with three 10 mL portions of dichloromethane. The organic layers were combined, dried ($MgSO_4$), and stripped to give a residue which was purified by PTLC (one 2 mm silica gel plate eluted with dichloromethane), affording 160 mg (73% yield) of 4-trifluoromethylaniline.

Orthohydrocarbyl perfluoroalkyl phenolic compounds such as 2-alkyl- and 2,6-dialkyl-4-perfluoroalkylphenols, 2-alkyl-4-perfluoroalkylnaphthols and 6-alkyl- and may be used as antioxidants and stablizers in polymers, lubricants and like substrates normally susceptible to oxidative deterioration during storage or use, and as intermediates for the synthesis of phosphites, phosphates, thiophosphites, thiophosphates, and like products which may be used as antioxidants and as agricultural chemicals. Exemplary orthohydrocarbyl perfluoroalkyl phenolic compounds of this type include:
2-methyl-4-perfluoromethylphenol
2-ethyl-4-perfluoromethylphenol
2-isopropyl-4-perfluoromethylphenol
2-tert-butyl-4-perfluoromethylphenol
2-(2-octyl)-4-perfluoromethylphenol
2-benzyl-4-perfluoromethylphenol
2-cyclopentyl-4-perfluoromethylphenol
2,6-dimethyl-4-perfluoromethylphenol
2,6-diethyl-4-perfluoromethylphenol
2,6-diisopropyl-4-perfluoromethylphenol
2,6-di-tert-butyl-4-perfluoromethylphenol
2-tert-butyl-6-methyl-4-perfluoromethylphenol
2-benzyl-6-methyl-4-perfluoromethylphenol
2-cyclopentyl-6-ethyl-4-perfluoromethylphenol
2-ethyl-4-perfluoroethylphenol
2-ethyl-4-perfluoropropylphenol
2-isopropyl-4-perfluoroethylphenol
2-tert-butyl-4-perfluoroethylphenol
2-(2-octyl)-4-perfluorobutylphenol
2,6-dimethyl-4-perfluoropentylphenol
2,6-diethyl-4-perfluoroethylphenol
2,6-diisopropyl-4-perfluoroisopropylphenol
2,6-di-tert-butyl-4-perfluoroethylphenol
2-tert-butyl-6-methyl-4-perfluorobutylphenol
2-methyl-4-perfluoromethylnaphthol
2-ethyl-4-perfluoromethylnaphthol
2-isopropyl-4-perfluoromethylnaphthol
2-tert-butyl-4-perfluoromethylnaphthol
2-(2-octyl)-4-perfluoromethylnaphthol
2-methyl-4-perfluoroethylnaphthol
2-ethyl-4-perfluoropropylnaphthol
2-isopropyl-4-perfluoroethylnaphthol
2-tert-butyl-4-perfluoroethylnaphthol
2-(2-octyl)-4-perfluorobutylnaphthol
2-benzyl-4-perfluoromethylnaphthol
2-cyclophentyl-4-perfluoromethylnaphthol
6-methyl-2-perfluoromethylphenol
6-ethyl-2-perfluoromethylphenol
6-isopropyl-2-perfluoromethylphenol
6-tert-butyl-2-perfluoromethylphenol
6-(2-decyl)-2-perfluoromethylphenol
6-benzyl-2-perfluoromethylphenol
6-cyclopentyl-2-perfluoromethylphenol
4,6-dimethyl-2-perfluoromethylphenol
4,6-diethyl-2-perfluoromethylphenol
4,6-diisopropyl-2-perfluoromethylphenol
4,6-di-tert-butyl-2-perfluoromethylphenol
4-tert-butyl-6-methyl-2-perfluoromethylphenol
4-benzyl-6-methyl-2-perfluoromethylphenol
4-cyclopentyl-6-ethyl-2-perfluoromethylphenol
4-ethyl-2-perfluoroethylphenol
4-ethyl-2-perfluoropropylphenol
4-isopropyl-2-perfluoroethylphenol
4-tert-butyl-2-perfluoroethylphenol
4-(2-dodecyl)-2-perfluorobutylphenol
4,6-dimethyl-2-perfluoropentylphenol
4,6-diethyl-2-perfluoroethylphenol
4,6-diisopropyl-2-perfluoroisopropylphenol
4,6-di-tert-butyl-2-perfluoroethylphenol
4-tert-butyl-6-methyl-2-perfluorobutylphenol Orthohydrocarbyl perfluoroalkyl aromatic amines such as 2-alkyl- and 2,6-dialkyl-4-perfluoroalkyl anilines, 2-alkyl-4-perfluoroalkyl-1-naphthyl amines, and 6-alkyl- and 4,6-dialkyl-2-perfluoroalkyl anilines are useful as intermediates for the synthesis of crop protection chemicals such as herbicides and plant growth regulants and as intermediates for the synthesis of pesticides such as insecticides, miticides, acaricides, and fungicides.

Exemplary orthohydrocarbyl perfluoroalkyl aromatic amines includes
2-methyl-4-perfluoromethylaniline
2-ethyl-4-perfluoromethylaniline 2-isopropyl-4-perfluoromethylaniline
2-tert-butyl-4-perfluoromethylaniline
2-(2-octyl)-4-perfluoromethylaniline
2-benzyl-4-perfluoromethylaniline
2-cyclopentyl-4-perfluoromethylaniline
2,6-dimethyl-4-perfluoromethylaniline
2,6-diethyl-4-perfluoromethylaniline
2,6-diisopropyl-4-perfluoromethylaniline
2,6-di-tert-butyl-4-perfluoromethylaniline
2-tert-butyl-6-methyl-4-perfluoromethylaniline
2-benzyl-6-methyl-4-perfluoromethylaniline
2-cyclopentyl-6-ethyl-4-perfluoromethylaniline
2-ethyl-4-perfluoroethylaniline
2-ethyl-4-perfluoropropylaniline
2-isopropyl-4-perfluoroethylaniline
2-tert-butyl-4-perfluoroethylaniline
2-(2-octyl)-4-perfluorobutylaniline
2,6-dimethyl-4-perfluoropentylaniline
2,6-diethyl-4-perfluoroethylaniline
2,6-diisopropyl-4-perfluoroisopropylaniline
2,6-di-tert-butyl-4-perfluoroethylaniline
2-tert-butyl-6-methyl-4-perfluorobutylaniline
2-methyl-4-perfluoromethyl-1-naphthylamine
2-ethyl-4-perfluoromethyl-1-naphthylamine
2-isopropyl-4-perfluoromethyl-1-naphthylamine
2-tert-butyl-4-perfluoromethyl-1-naphthylamine
2-(2-octyl)-4-perfluoromethyl-1-naphthylamine
2-methyl-4-perfluoroethyl-1-naphthylamine
2-ethyl-4-perfluoropropyl-1-naphthylamine
2-isopropyl-4-perfluoroethyl-1-naphthylamine
2-tert-butyl-4-perfluoroethyl-1-naphthylamine
2-(2-octyl)-4-perfluorobutyl-1-naphthylamine
2-benzyl-4-perfluoromethyl-1-naphthylamine
2-cyclopentyl-4-perfluoromethyl-1-naphthylamine
6-methyl-2-perfluoromethylaniline
6-ethyl-2-perfluoromethylaniline
6-isopropyl-2-perfluoromethylaniline
6-tert-butyl-2-perfluoromethylaniline
6-(2-decyl)-2-perfluoromethylaniline
6-benzyl-2-perfluoromethylaniline
6-cyclopentyl-2-perfluoromethylaniline
4,6-dimethyl-2-perfluoromethylaniline
4,6-diethyl-2-perfluoromethylaniline
4,6-diisopropyl-2-perfluoromethylaniline
4,6-di-tert-butyl-2-perfluoromethylaniline
4-tert-butyl-6-methyl-2-perfluoromethylaniline
4-benzyl-6-methyl-2-perfluoromethylaniline
4-cyclopentyl-6-ethyl-2-perfluoromethylaniline
4-ethyl-2-perfluoroethylaniline
4-ethyl-2-perfluoropropylaniline
4-isopropyl-2-perfluoroethylaniline
4-tert-butyl-2-perfluoroethylaniline
4-(2-dodecyl)-2-perfluorobutylaniline p0 4,6-dimethyl-2-perfluoropentylaniline
4,6-diethyl-2-perfluoroethylaniline
4,6-diisopropyl-2-perfluoroisopropylaniline
4,6-di-tert-butyl-2-perfluoroethylaniline
4-tert-butyl-6-methyl-2-perfluorobutylaniline Still other products which may be produced from the gem-dicyclohexadienones of this invention include (i) novel gem-disubstituted cyclohexadienones in which the gem-substitutents are a perfluoroalkyl group and a hydroxyl group, (ii) novel gem-disubstituted cyclohexanones in which the gem-substituents are a perfluoroalkyl group and a trihydrocarbylsiloxy group, (iii) novel gem-disubstituted cyclohexanols in which the gem-substituents are a perfluoroalkyl group and a trihydrocarbylsiloxy group, and (iv) novel gem-disubstituted cyclohexanones in which the gem-substituents are a perfluoroalkyl group and a hydroxyl group. Methods for effecting the synthesis of such compounds are illustrated in Examples XXI through XXX below.

EXAMPLE XXI

4-Hydroxy-4-trifluoromethyl-2,5-cyclohexadien-1-one

A mixture of 200 mg (0.68 mmol) of 4-triethylsiloxy-4-trifluoromethyl-2,5-cyclohexadien-1-one and 1 mL of a solution of 1 part 37% hydrochloric acid in 9 parts absolute ethanol was heated at reflux overnight and poured into 10 mL of water. The resulting aqueous mixture was extracted with three 10 mL portions of dichloromethane. Combination, drying (MgSO$_4$), and concentration of the organic layers afforded a residue which was purified by PTLC (one 2 mm silica gel plate eluted with 1% methanol - 99% dichloromethane) to give 109 mg (89% yield) of 4-hydroxy-4-trifluoromethyl-2,5-cyclohexadien-1-one. An analytical sample was obtained by crystallization from dichloromethane-hexane: mp 84°–86° C.; $^1$H NMR (CDCl$_3$) δ 3.40 (broad s,1H), 6.40 (d, 2H, J=10 Hz), 6.89 (d, 2H, J=10 Hz); $^{13}$C NMR (CDCl$_3$) 70.2 (q, $J_{CF}$=30 Hz), 125.0 (q, $J_{CF}$=286 Hz), 132.2 (d), 142.7 (d), 184.5 (s) ppm; $^{19}$F NMR (CDCl$_3$) relative to CFCl$_3$) −79.6 ppm (s); IR (KBr) 3374, 3105, 3022, 2919, 1693, 1671, 1632, 1620, 1396, 1249, 1235, 1195, 1174, 1089, 1078, 1003, 988, 980, 973, 863, 698 cm$^{-1}$; mass spectrum (70 eV) m/z (relative intensity) 178 (5, M+), 109 (100), 81 (34), 53 (36). Anal. Calcd. for C$_7$H$_5$F$_3$O$_2$: C, 47.20; H, 2.83. Found: C, 47.42; H, 2.80.

In Examples XXII through XXVII procedures as described in Example XXI were used.

EXAMPLE XXII

4-Hydroxy-4-trifluoromethyl-2,5-cyclohexadien-1-one

From 300 mg (0.80 mmol) of 4-tri-n-butylsiloxy-4-trifluoromethyl-2,5-cyclohexadien-1-one was obtained a product mixture. Gas chromatographic/mass spectral analysis showed that the major component of this mixture was 4-hydroxy-4-trifluoromethyl-2,5-cyclohexadien-1-one.

EXAMPLE XXIII 2,6-Di-tert-butyl-4-hydroxy-4-trifluoromethyl-2,5-cyclohexadien-1-one From 350 mg (0.87 mmol) of 2,6-di-tert-butyl-4-triethylsiloxy-4-trifluoromethyl-2,5-cyclohexadien-1-one was obtained a product mixture which was purified by PTLC (one 2 mm silica gel plate eluted with dichloromethane) to give 245 mg (98% yield) of 2,6-di-tert-butyl-4-hydroxy-4-trifluoromethyl-2,5-cyclohexadien-1-one. An analytical sample was obtained by crystallization from hexane: mp 93–94° C.; $^1$H NMR (CDCl$_3$) δ 1.25 (s, 18H), 2.57 (s, 1H), 6.48 (s, 2H); $^{19}$F NMR (CDCl$_3$, relative to CFCl$_3$) −79.8 to −79.9 ppm (m); IR (KBr) 3374, 3103, 3022, 2919, 1693, 1671, 1632, 1620, 1396, 1249, 1235, 1195, 1174, 1089, 1078, 1003, 988, 980, 973, 863, 698 cm$^{-1}$; mass spectrum (70 eV) m/z (relative intensity) 290 (7, M+), 275 (18), 247 (20), 57 (100), 43 (35), 41 (62). Anal. Calcd. for C$_{15}$H$_{12}$F$_3$O$_2$: C, 62.05; H, 7.29. Found: C, 61.98; H, 7.46.

EXAMPLE XXIV

4,6-Di-tert-butyl-2-hydroxy-2-trifluoromethyl-3,5-cyclohexadien-1-one

From 350 mg (0.87 mmol) of 4,6-di-tert-butyl-2-triethylsiloxy-2-trifluoromethyl-3,5-cyclohexadien-1-one was obtained a product mixture which was purified by PTLC (one 2 mm silica gel plate eluted with 20% dichloromethane - 80% petroleum ether) to give 218 mg (87% yield) of 4,6-di-tert-butyl-2-hydroxy-2-trifluoromethyl-3,5-cyclohexadien-1-one. An analytical sample was obtained by crystallization from hexane: mp 58°–61° C.; $^1$H NMR (CDCl$_3$) δ 1.17 (s, 9H), 1.25 (s, 9H), 4.32 (s, 1H), 5.96 (d, 1H, J=2 Hz), 6.93 (d, 1H, J=2 Hz); $^{19}$F NMR (CDCl$_3$, relative to CFCl$_3$) −79.5 ppm (s); IR (KBr) 3456, 2964, 1676, 1372, 1367, 1254, 1234, 1217, 1186, 1163, 1151, 1124, 694 cm$^{-1}$; mass spectrum (70 eV) m/z (relative intensity) 290 (12, M+), 275 (20), 205 (28), 69 (30), 57 (100), 43 (27), 41 (77), 39 (20), Anal. Calcd. for C$_{15}$H$_{12}$F$_3$O$_2$: C, 62.05; H, 7.29. Found: C, 62.16; H, 7.27.

EXAMPLE XXV

9.10-Dihydro-10-hydroxy-9-oxo-10-trifluoromethylnaphthalene

From 350 mg (1.0 mmol) of 9,10-dihydro-9-oxo-10-triethylsiloxy-10-trifluoromethylnaphthalene was obtained a product mixture which was purified by PTLC (one 2 mm silica gel plate eluted with 1% methanol - 99% dichloromethane) to give 192 mg of 89% pure (73% yield) 9,10-dihydro-10-hydroxy-9-oxo-10-trifluoromethylnaphthalene. An analytical sample was obtained by crystallization from dichloromethane-hexane: mp 73°–76° C.; $^1$H NMR (CDCl$_3$) δ 3.94 (s, 1H), 6.48 (d, 1H, J=10 Hz), 7.02 (d, 1H, J =10 Hz), 7.43–8.18 (m, 4H); $^{19}$F NMR (CDCl$_3$, relative to CFCl$_3$) −80.0 ppm (s); IR(KBr) 3368, 1667, 1627, 1597, 1454, 1377, 1301, 1283, 1230, 1188, 1172, 1156, 1142, 1102, 1047, 1017, 935, 838, 769, 754, 603, 560 cm$^{-1}$; mass spectrum (70 eV) m/z (relative intensity) 228 (8, M+), 159 (100), 131 (30), 103 (22), 77 (25). Anal. Calcd. for C$_{11}$H$_7$F$_3$O$_2$ C, 57.90; H, 3.09. Found: C, 57.94; H, 3.12.

EXAMPLE XXVI

9,10-Dihydro-10-hydroxy-9-oxo-10-trifluoromethylanthracene

From 340 mg (0.89 mmol) of 9,10-dihydro-9-oxo-10-triethylsilyolxy-10-trifluoromethylanthracene was obtained a product mixture which was purified by PTLC (one 2 mm silica gel plate eluted with dichloromethane) to give 223 mg (90% yield) of 9,10-dihydro-10-hydroxy-9-oxo-10-trifluoromethylanthracene. An analytical sample was obtained by crystallization from dichloro- methane-hexane: mp 153°–155° C.; $^1$H NMR (CDCl$_3$) δ 3.56 (s, 1H), 7.47–7.82 (m, 4H), 7.92–8.31 (m, 4H); $^{19}$F NMR (CDCl$_3$, relative to CFCl$_3$) −79.8 ppm (s); IR (KBr) 3417, 1656, 1598, 1584, 1458, 1320, 1269, 1219, 1165, 1128, 1062, 933, 764, 716 cm$^{-1}$; mass spectrum (70 eV) m/z (relative intensity) 278 (1, M+), 209 (100), 152 (24). Anal. Calcd. for C$_{15}$H$_9$F$_3$O$_2$:C, 64.75; H, 3.26. Found: C, 64.63; H, 3.29.

EXAMPLE XXVII

9,10-Dihydro-10-hydroxy-9-oxo-10-trifluoromethylohenanthrene

From 350 mg (0.89 mmol) of 9,10-dihydro-9-oxo-10-tri- ethylsiloxy-10-trifluoromethylphenanthrene was obtained a product mixture that was purified by PTLC (one 2 mm slica gel plate eluted with 50% dichloromethane - 50% petroleum ether) to give 238 mg (96% yield) of 9,10-dihydro-10-hydroxy-9-oxo-10-trifluoromethylphenanthrene. An analytical sample was obtained by crystallization from dichloromethane-hexane: mp 148°–151° C.; $^1$H NMR (CDCl$_3$) δ 4.76 (s, 1H), 7.22–8.07 (m, 8H); $^{19}$F NMR (CDC$_3$ relative to CFCl$_3$) −78.5 ppm (s); IR (KBr) 3455, 1687, 1598, 1479, 1451, 1321, 1299, 1286, 1228, 1210, 1167, 1110, 1056, 1015, 956, 941, 905, 778, 758, 731, 641, 615 cm$^{-1}$; mass spectrum (70 eV) m/z (relative intensity) 278 (31, M+), 209 (100), 181 (43), 152 (34), 75 (33). Anal. Calcd. for C$_{15}$H$_9$F$_3$O$_2$: C, 64.75; H, 3.26. Found: C, 64.75; H, 3.30.

EXAMPLE XXVIII

4-Triethylsiloxy-4-trifluoromethylcyclohexanone

A solution of 291 mg of 4-triethylsiloxy-4-trifluoromethyl-2,5-cyclohexadien-1-one in 2 mL of absolute ethanol was treated with a few mg of 5% palladium on carbon, hydrogenated in a Parr shaker for one hour under 50 psig of hydrogen, and filtered. Concentration of the filtrate gave 4-triethylsiloxy-4-trifluoromethylcyclohexanone: $^1$H NMR (CDCl$_3$) δ 0.45–1.16 (m, 15H), 1.92–2.89 (m, 8H); mass spectrum (70 eV) m/z (relative intensity) 267 (19, M-C$_2$H$_5$), 115 (45), 105 (33), 87 (100), 81 (22), 77 (67), 73 (20), 67 (29), 59 (57), 55 (84), 47 (20).

EXAMPLE XXIX

9,10-Dihydro-9-hydroxy-10-triethylsiloxy-10-trifluoromethylanthracene

A solution of 50 mg (0.13 mmol) of 9,10-dihydro-9-oxo-10-triethylsiloxy-10-trifluoromethylanthracene in 0.5 mL of absolute ethanol was treated successively with 42 mg (0.65 mmol) of zinc dust and 0.5 mL of a solution of 90% acetic acid - 20% water. The mixture was heated to reflux in a 110° C. oil bath for 2 hours, allowed to cool to room temperature, and poured into 10 mL of water. The resulting aqueous mixture was extracted with three 5 mL portions of diethyl ether. Combination, drying, and concentration of the ether layers gave a residue which was purified by PTLC (one 1 mm silica gel plate eluted with 50% dichloromethane 50% petroleum ether) to give 34 mg of 87% pure (58% yield) 9,10-dihydro-9-hydroxy-10-triethysiloxy-10-trifluoromethylanthracene as a white solid: mass spectrum (70 eV) m/z (relative intensity) 363 (8, M-C$_2$H$_5$), 211 (100), 183 (21), 77 (25); TMS derivative 466 (M+), 368 (27), 246 (24), 196 (22), 193 (90), 165 (21), 105 (40), 87 (28), 77 (47), 73 (100), 59 (20), 45 (21).

EXAMPLE XXX

4-Hydroxy-4-trifluoromethylcyclohexanone

A solution of 100 mg of 4-hydroxy-4-trifluoromethyl-2,5-cyclohexadien-1-one in 1 mL of absolute ethanol was treated with a few mg of 5% palladium on carbon, hydrogenated in a Parr shaker for one hour under 50 psig of hydrogen, and filtered. Gas chromatographic/-mass spectral analysis indicated that the major component of the filtrate was 4-hydroxy-4-trifluoromethylcyclohexanone: mass spectrum (70 eV) m/z (relative intensity) 182 (11, M+), 55 (100), 42 (40).

This invention is susceptible to considerable variation within the spirit and scope of the appended claims and thus is not intended to be limited by the exemplifications herein provided.

What is claimed is:

1. A process which comprises reacting under essentially anhydrous conditions a quinone with a perfluoroalkyltrihydrocarbylsilane in the presence of an active alkali metal salt catalyst devoid of fluorine so that a gem-disubstituted cyclohexadienone is produced.

2. A process of claim 1 conducted in a liquid phase reaction medium.

3. A process of claim 1 wherein the quinone is a 1,4-quinone.

4. A process of claim 3 wherein the 1,4-quinone is a mononuclear 1,4-quinone.

5. A process of claim 3 wherein the 1,4-quinone is a polynuclear 1,4-quinone.

6. A process of claim 3 wherein the 1,4-quinone is a polynuclear fused ring 1,4-quinone.

7. A process of claim 1 wherein the quinone is a 1,2-quinone.

8. A process of claim 7 wherein the 1,2-quinone is a mononuclear 1,2-quinone.

9. A process of claim 7 wherein the 1,2-quinone is a polynuclear fused ring 1,2-quinone.

10. A process of claim 1 wherein the perfluoroalkyltrihydrocarbylsilane is a perfluoroalkyltrialkylsilane.

11. A process of claim 1 wherein the perfluoroalkyltrihydrocarbylsilane is a trifluoromethyltrihydrocarbylsilane.

12. A process of claim 1 wherein the perfluoroalkyltrihydrocarbysilane is a trifluoromethyltrialkylsilane.

13. A process of claim 1 wherein the catalyst is potassium carbonate.

14. A process of claim 1 wherein the catalyst is sodium cyanide or potassium cyanide, or both.

15. A process of claim 1 wherein the catalyst is an alkali metal azide.

16. A process of claim 1 wherein the catalyst is sodium hydroxide or potassium hydroxide, or both.

17. A process of claim 1 wherein the reaction is performed in a liquid dipolar aprotic reaction medium.

18. A process of claim 1 wherein the reaction is performed in a liquid reaction medium comprising N,N-dimethylformamide, N,N-dimethylacetamide, sulfolane or acetonitrile.

19. A process of claim 1 wherein the reaction is performed in a liquid reaction medium consisting essentially of acetonitrile and wherein the catalyst is potassium cyanide.

20. A process of claim 1 wherein the reaction is performed in a liquid reaction medium consisting essentially of acetonitrile and wherein the catalyst is potassium carbonate.

21. A process of claim 1 wherein the reaction is performed in a liquid reaction medium consisting essentially of N,N-dimethylformamide and wherein the catalyst is potassium carbonate.

22. A process of claim 1 wherein the temperature is maintained in the range of about 0° to about 25° C. throughout substantially the entire reaction.

23. A process which comprises reacting under essentially anhydrous conditions in a liquid phase reaction medium a 1,2- or 1,4-quinone with a trifluoromethyltrihydrocarbylsilane in the presence of an active alkali metal salt catalyst devoid of fluorine so that a gem-disubstituted cyclohexadienone is produced.

24. A process of claim 23 wherein said catalyst is (a) potassium carbonate or cesium carbonate, or both, (b) sodium cyanide or potassium cyanide, or both (c) an alkali metal azide, (d) sodium hydroxide or potassium hydroxide, or both, or any mixture of any two, or any three or all four of (a), (b), (c) and (d)

25. A process of claim 24 wherein the reaction medium comprises N,N-dimethylformamide, N,N-dimethylacetamide, sulfolane or acetonitrile.

26. A process of claim 23 wherein the temperature is maintained in the range of about 0° to about 25° C. throughout substantially the entire reaction.

27. A process of claim 23 wherein the reaction is performed in a liquid reaction medium consisting essentially of acetonitrile and wherein the catalyst is potassium cyanide.

28. A process of claim 23 wherein the reaction is performed in a liquid reaction medium consisting essentially of acetonitrile and wherein the catalyst is potassium carbonate.

29. A process of claim 23 wherein the reaction is performed in a liquid reaction medium consisting essentially of N,N-dimethylformamide and wherein the catalyst is potassium carbonate.

30. A process of claim 23 wherein the trifluoromethyltrihydrocarbylsilane is a trifluoromethyltrialkylsilane; wherein said catalyst is potassium cyanide or potassium carbonate, or both; wherein the reaction medium consists essentially of N,N-dimethylformamide, N,N-dimethylacetamide, sulfolane or acetonitrile; and wherein the temperature is maintained in the range of about 0° to about 25° C. throughout substantially the entire reaction.

31. A gem-disubstituted cyclohexadienone in which the gem-substituents are a perfluoroalkyl group and a trihydrocarbysiloxy group.

32. A composition of claim 31 wherein the perfluoroalkyl group is a trifluoromethyl group.

33. A composition of claim 31 wherein the trihydrocarbylsiloxy group is a trialkylsiloxy group.

34. A composition of claim 31 wherein the perfluoroalkyl group is a trifluoromethyl group and the trihydrocarbylsiloxy group is a trialkylsiloxy group.

35. A composition of claim 31 wherein said gem substitutents are in the para-position relative to the keto group of the dienone.

36. A composition of claim 35, namely a 4-trialkylsiloxy-4-trifluoromethyl-2,5-cyclohexadien-1-one.

37. A composition of claim 35, namely 4-triethylsiloxy-4trifluoromethyl-2,5-cyclohexadien-1-one.

38. A composition of claim 35, namely 4-tributylsiloxy-4-trifluoromethyl-2,5-cyclohexadien-1-one.

39. A composition of claim 35, namely a 4-trialkylsiloxy-4-trifuoromethyl-2,5-cyclohexadien-1-one having an alkyl substituent in at least the two or six position.

40. A composition of claim 35, namely 2,6-di-tert-butyl-4-triethylsiloxy-4-trifluoromethyl-2,5-cyclohexadien-1-one.

41. A composition of claim 35, namely a 1,4-dihydro-1-oxo-4-trialkylsiloxy-4-trifluoromethylnaphthalene.

42. A composition of claim 35, namely 1,4-dihydro-1-oxo-4-triethylsiloxy-4-trifluoromethylnaphthalene.

43. A composition of claim 35, namely a 9,10-dihydro-9-oxo-10-trialkylsiloxy-10-trifluoromethylanthracene.

44. A composition of claim 35, namely 9,10-dihydro-9-oxo-10-triethylsiloxy-10-trifluoromethylanthracene.

45. A composition of claim 31 wherein said gem-substitutents are in the ortho-position relative to the keto group of the dienone.

46. A composition of claim 45, namely a 2-trialkylsiloxy-2-trifluoromethyl-2,4-cyclohexadien-1-one.

47. A composition of claim 45, namely a 2-trialkylsiloxy-2-trifluoromethyl-3,5-cyclohexadien-1-one having an alkyl substituent in at least the four or six position.

48. A composition of claim 45, namely 4,6-di-tert-butyl-2-triethylsiloxy-2-trifluoromethyl-3,5-cyclohexadien-1-one.

49. A composition of claim 45, namely a 9,10-dihydro-9-oxo-10-trialkylsiloxy-10-trifluoromethylphenanthrene.

50. A composition of claim 45, namely 9,10-dihydro-9-oxo-10-triethylsiloxy-10-trifluoromethylphenanthrene.

* * * * *